US012329181B2

(12) United States Patent
Jury et al.

(10) Patent No.: US 12,329,181 B2
(45) Date of Patent: Jun. 17, 2025

(54) MICROBIAL FEED SUPPLEMENT COMPOSITION AND METHOD

(71) Applicant: Terragen Holdings Limited, Coolum Beach (AU)

(72) Inventors: Karen Jury, Coolum Beach (AU); Martin Soust, Coolum Beach (AU)

(73) Assignee: Terragen Holdings Limited, Coolum Beach (AU)

( * ) Notice: Subject to any disclaimer, the term of this patent is extended or adjusted under 35 U.S.C. 154(b) by 30 days.

(21) Appl. No.: 17/185,256

(22) Filed: Feb. 25, 2021

(65) Prior Publication Data

US 2021/0267232 A1    Sep. 2, 2021

(30) Foreign Application Priority Data

Feb. 28, 2020   (AU) ................. 2020201488

(51) Int. Cl.
| | | |
|---|---|---|
| *A23K 10/18* | (2016.01) | |
| *A23K 20/163* | (2016.01) | |
| *A23K 50/10* | (2016.01) | |
| *A23K 50/60* | (2016.01) | |
| *A61K 35/747* | (2015.01) | |

(52) U.S. Cl.
CPC ............ *A23K 10/18* (2016.05); *A23K 20/163* (2016.05); *A23K 50/10* (2016.05); *A23K 50/60* (2016.05); *A61K 35/747* (2013.01); *A23V 2400/125* (2023.08); *A23V 2400/165* (2023.08)

(58) Field of Classification Search
None
See application file for complete search history.

(56) References Cited

FOREIGN PATENT DOCUMENTS

| | | | | |
|---|---|---|---|---|
| WO | WO-2012110777 A2 | * | 8/2012 | ............ A23K 10/18 |
| WO | WO-2018187838 A1 | * | 10/2018 | ............ A61K 35/747 |
| WO | WO-2019178309 A1 | * | 9/2019 | ............ A23K 10/18 |

OTHER PUBLICATIONS

Cambridge University Press. "Syrup". In Cambridge dictionary. Online. Retrieved Nov. 30, 2022 (Year: 2022).*
Frizzo et al., "Effects of probiotics on growth performance in young calves: A meta-analysis of randomized controlled trials", Animal Feed Science and Technology, vol. 169, p. 147-156. (Year: 2011).*
Drissi, F., et al., "Metabolic role of lactobacilli in weight modification in humans and animals", Microbial Pathogenesis, vol. 106, pp. 182-194. (Year: 2017).*
Timmerman, et al., "Health and Growth of Veal Calves Fed Milk Replacers With or Without Probiotics", Journal of Dairy Science, vol. 88(6), pp. 2154-2165 (Year: 2005).*
Frizzo et al., "The Effect of Supplementation with Three Lactic Acid Bacteria from Bovine Origin on Growth Performance and Health Status of Young Calves", Journal of Animal and Veterinary Advances, vol. 7(4), pp. 400-408. (Year: 2008).*
Carroll, Bernard J., David L. McNeil, and Peter M. Gresshoff. "Isolation and properties of soybean [*Glycine max* (L.) Merr.] mutants that nodulate in the presence of high nitrate concentrations." Proceedings of the National Academy of Sciences 82.12 (1985): 4162-4166.
Men, Artem E., et al. "Fast neutron mutagenesis of soybean (*Glycine soja* L.) produces a supernodulating mutant containing a large deletion in linkage group H." Genome letters 1.3 (2002): 147-155.
Chapter 19.3 "Detection of Helper Virus in Retrovirus Stocks" of Current Protocols in Molecular Biology, Ausubel, F. M., B. Roger, R. E. Kingston, D. D. Moore, J. G. Seidman, J. A. Smith, and S. Kevin, 2003.
Chapter 9 "Introduction of DNA Into Mammalian Cells" of Current Protocols in Molecular Biology, Ausubel, F. M., B. Roger, R. E. Kingston, D. D. Moore, J. G. Seidman, J. A. Smith, and S. Kevin, 2003.

* cited by examiner

*Primary Examiner* — Michelle F. Paguio Frising
*Assistant Examiner* — Grant C Currens
(74) *Attorney, Agent, or Firm* — Meunier Carlin & Curfman LLC

(57) ABSTRACT

A composition for administration to an animal is provided. The composition comprises a bacteria of the genus *Lactobacillus*. Also provided is a method of improving or enhancing one or more characteristics of an animal by administering a composition comprising a bacteria of the genus *Lactobacillus* to the animal. The animal may be cattle, such as a calf. Related animals and animal products are further provided.

14 Claims, 7 Drawing Sheets

Specification includes a Sequence Listing.

MICROBIAL FEED SUPPLEMENT COMPOSITION AND METHOD

CROSS-REFERENCE TO RELATED APPLICATIONS

This application claims the benefit of Australian Patent Application No. 2020201488 filed Feb. 28, 2020 in the Australian Patent Office, and New Zealand Patent Application No. 762186 filed Feb. 28, 2020, in the New Zealand Patent Office, the entire disclosure of which is incorporated herein by reference.

REFERENCE TO AN ELECTRONIC SEQUENCE LISTING

The content of the electronic sequence listing submitted on Feb. 25, 2021, as a text file named "11181-007US1_Patentin_Project_ST25.txt" created on Feb. 1, 2021, and having a size of 33,171,000 bytes, is herein incorporated by reference in its entirety in accordance with the requirements of 37 CFR 1.821-1.825.

TECHNICAL FIELD

The present invention relates to a microbial composition. More particularly, the invention relates to a composition comprising *Lactobacillus* bacteria suitable for use as a feed supplement for animals, typically ruminants, although without limitation thereto. The invention also relates to methods of promoting animal growth, development, and/or productivity, typically ruminant growth, development, and/or productivity, using a microbial composition comprising *Lactobacillus* bacteria.

BACKGROUND

Farmed ruminants including cattle, sheep, and goats are commonly raised for the purpose of production of commodities such as meat, milk, leather, and wool. Among the ruminants, cattle are of the greatest economic significance with beef and dairy cattle industries worth billions of dollars worldwide.

A critical consideration for farming of animals, including ruminants, is production efficiency. Various circumstances may influence production efficiency from animals, however animal nutrition is typically a key factor. Supplements, including feed supplements, have been developed to attempt to improve nutrition of farmed animals.

Ruminant animals possess highly specialised digestive systems, including a complex mix of microbes that assist with the digestive process. Accordingly, the development of supplements, particularly feed supplements, for ruminants is associated with significant challenges and there is presently a need for new such supplements. It would be particularly desirable if such supplements showed efficacy for improving productivity from cattle, such as efficiency of meat or milk production. It would also be particularly desirable, in at least some circumstances, if such supplements were amenable to controlled dosing through voluntary consumption by animals.

The reference to prior art in the background is not and should not be taken as an acknowledgement or any form of suggestion that the referenced prior art forms part of the common general knowledge.

SUMMARY

A first aspect of the invention is broadly directed to a composition comprising one or more bacteria of the genus *Lactobacillus*. In embodiments, the composition comprises a plurality of bacteria of the genus *Lactobacillus*.

Suitably, the composition of the first aspect is for administration to an animal. Suitably, the composition of the first aspect is for administration to an animal to improve one or more of nutrition, growth, development, and/or productivity of the animal.

In embodiments, the composition of the first aspect is for administration to a ruminant animal. In an embodiment, the composition is for administration to cattle.

Suitably, the composition of the first aspect is an animal supplement. In embodiments, the composition of the first aspect is a ruminant animal supplement.

In embodiments, the one or more bacteria of the genus *Lactobacillus* of the composition of the first aspect are of a species selected from *Lactobacillus paracasei*, *Lactobacillus buchneri*, and *Lactobacillus casei*.

In embodiments, the composition of the first aspect comprises at least two bacterial species selected from *Lactobacillus paracasei*, *Lactobacillus buchneri*, and *Lactobacillus casei*.

In an embodiment, the composition comprises a bacteria of the species *Lactobacillus paracasei* and a bacteria of the species *Lactobacillus buchneri*.

In an embodiment, the composition comprises a bacteria of the species *Lactobacillus paracasei* and a bacteria of the species *Lactobacillus casei*.

In an embodiment, the composition comprises a bacteria of the species *Lactobacillus buchneri* and a bacteria of the species *Lactobacillus casei*.

In an embodiment, the composition comprises a bacteria of the species *Lactobacillus paracasei*, a bacteria of the species *Lactobacillus buchneri*, and a bacteria of the species *Lactobacillus casei*.

In an embodiment of the first aspect wherein the composition comprises a bacteria of the species *Lactobacillus paracasei*, the bacteria is *Lactobacillus paracasei* strain T9 as deposited with the National Measurement Institute, Australia, on 14 Dec. 2012 under Accession Number V12/022849 (*Lactobacillus paracasei* T9 V12/022849), in accordance with the terms of the Budapest Treaty with the American Type Culture Collection (ATCC), Manassas, Virginia.

In an embodiment of the first aspect wherein the composition comprises a bacteria of the species *Lactobacillus buchneri*, the bacteria is *Lactobacillus buchneri* strain Lb23 as deposited with the National Measurement Institute, Australia, on 27 Oct. 2011 under Accession Number V11/022946 (*Lactobacillus buchneri* Lb23 V11/022946), in accordance with the terms of the Budapest Treaty with the American Type Culture Collection (ATCC), Manassas, Virginia.

In an embodiment of the first aspect wherein the composition comprises a bacteria of the species *Lactobacillus casei*, the bacteria is *Lactobacillus casei* strain Lz26 as deposited with the National Measurement Institute, Australia, on 27 Oct. 2011 under Accession Number V11/022948 (*Lactobacillus casei* Lz26 V11/022948), in accordance with the terms of the Budapest Treaty with the American Type Culture Collection (ATCC), Manassas, Virginia.

The bacteria of the genus *Lactobacillus* of the composition of the first aspect may comprise a genome comprising a nucleotide sequence set forth in SEQ ID NOS:1-383, or a fragment or variant thereof.

In embodiments, the genome of the bacteria of the genus *Lactobacillus* comprises a nucleotide sequence set forth in SEQ ID NOS:1-160, or a fragment or variant thereof. The bacteria may be of the species *Lactobacillus paracasei*.

In embodiments, the genome of the bacteria of the genus *Lactobacillus* comprises a nucleotide sequence set forth in SEQ IN NOS:161-292, or a fragment or variant thereof. The bacteria may be of the species *Lactobacillus buchneri*.

In embodiments, the genome of the bacteria of the genus *Lactobacillus* of the composition of the first aspect comprises a nucleotide sequence set forth in SEQ IN NOS:293-383, or a fragment or variant thereof. The bacteria may be of the species *Lactobacillus casei*.

The bacteria of the genus *Lactobacillus* of the composition of the first aspect may comprise a genome encoding an amino acid sequence set forth in SEQ ID NOS:384-8830, or a fragment or variant thereof.

In embodiments, the bacteria of the genus *Lactobacillus* comprises a genome encoding an amino acid sequence set forth in SEQ ID NOS:384-3504, or a fragment or variant thereof. The bacteria may be of the species *Lactobacillus paracasei*.

In embodiments, the bacteria of the genus *Lactobacillus* comprises a genome encoding an amino acid sequence set forth in SEQ ID NOS:3505-6021, or a fragment or variant thereof. The bacteria may be of the species *Lactobacillus buchneri*.

In embodiments, the bacteria of the genus *Lactobacillus* comprises a genome encoding an amino acid sequence set forth in SEQ ID NOS:6022-8828, or a fragment or variant thereof. The bacteria may be of the species *Lactobacillus casei*.

In embodiments, the total concentration of bacteria of the genus *Lactobacillus* of the composition of the first aspect is at least about $10^5$ colony-forming units per millilitre (CFU/ml) or colony-forming units per gram (CFU/g), at least about $10^6$ CFU/ml or CFU/g, at least about $10^7$ CFU/ml or CFU/g, at least about $10^8$ CFU/ml or CFU/g, or at least about $10^9$ CFU/ml or CFU/g.

In embodiments, the concentration of each bacteria of the genus *Lactobacillus* of the composition of the first aspect is at least about $10^5$ CFU/ml or CFU/g, at least about $10^6$ CFU/ml or CFU/g, at least about $10^7$ CFU/ml or CFU/g at least about $10^8$ CFU/ml or CFU/g, or at least about $10^9$ CFU/ml or CFU/g.

The composition of the first aspect may comprise a sugar or sugar syrup. In an embodiment, the sugar syrup is molasses. In embodiments, the sugar or sugar syrup is at a concentration of between about 1% weight per weight (w/w) or volume/volume (v/v) and about 10% w/w or v/v. In embodiments, the sugar or sugar syrup is at a concentration of at least about 1% w/w or v/v, at least about 2% w/w or v/v, at least about 3% w/w or v/v, at least about 4% w/w/ or v/v, or at least about 5% w/w/ or v/v.

The composition of the first aspect may comprise an acid. In an embodiment, the acid is an organic acid. In an embodiment, the acid is fulvic acid. In embodiments, the acid is at a concentration of between about 0.1% w/w or v/v and about 0.6% w/w or v/v. In embodiments, the acid is at a concentration of at least about 0.1% w/w or v/v, at least about 0.2% w/w or v/v, at least about 0.3% w/w or v/v, at least about 0.4% w/w or v/v, or at least about 0.5% w/w or v/v.

In embodiments, the composition of the first aspect is a liquid composition. In embodiments, the composition is an aqueous composition.

A second aspect of the invention provides a method of supplementing an animal, including a step of administering a composition comprising a bacteria of the genus *Lactobacillus* to the animal.

A third aspect of the invention provides a method of improving or enhancing one or more characteristics of an animal, including a step of administering a composition comprising a bacteria of the genus *Lactobacillus* to the animal.

In embodiments, the animal according to the method of the second or third aspect is a ruminant animal. In embodiments, the ruminant animal is selected from cattle, sheep, and goats. In an embodiment, the ruminant animal is cattle. In an embodiment, the cattle is a calf.

In embodiments, the step of administering the composition to the animal according to the method of the second or third aspect is or includes administering the composition to the digestive system of the animal. In embodiments, the composition is consumed voluntarily by the animal, whereby the composition is administered to the digestive system of the animal.

In an embodiment, the step of administering the composition to the animal according to the method of the second or third aspect includes combining the composition with feed, including food and/or drink, for consumption by the animal.

In embodiments of the third aspect, the one or more characteristics of the animal that are improved or enhanced are selected from nutrition, growth, development, and productivity. In an embodiment, the improved growth is greater total weight of the animal. In an embodiment, the improved development is greater gut structure development of the animal. In an embodiment, the improved productivity is improved meat production from the animal. In an embodiment, the improved productivity is improved milk production from the animal.

Suitably, the composition administered to the animal according to the second or third aspect is the composition of the first aspect.

A fourth aspect of the invention provides a supplemented animal produced according to the method of the second aspect.

A fifth aspect of the invention provides an animal with improved nutrition, growth, development, and/or productivity produced according to the method of the third aspect.

A sixth aspect of the invention provides an animal product derived from the animal of the fourth or fifth aspect. In embodiments, the animal product is a meat product or a dairy product.

A seventh aspect of the invention provides a method of combining a composition of the first aspect with an animal feed.

An eighth aspect of the invention provides an animal feed comprising the composition of the first aspect.

A ninth aspect of the invention provides a method of preparing a composition for administration to an animal, including the step of combining a *Lactobacillus* bacteria with one or more other components. In embodiments, the method of the ninth aspect is a method of preparing a composition for administration to a ruminant animal, such as cattle. In embodiments, the composition prepared according to the method of the ninth aspect is a composition of the first aspect.

A tenth aspect of the invention provides a method of preparing or storing a composition for administration to an animal, including a step of applying a treatment and/or a substance or agent to a *Lactobacillus* bacteria or a composition comprising a *Lactobacillus* bacteria. In embodiments of the tenth aspect, the step of applying a treatment to a *Lactobacillus* bacteria or a composition comprising a *Lactobacillus* bacteria is a step of freeze-drying the bacteria or composition. In embodiment, the step of applying a substance or agent to a *Lactobacillus* bacteria or a composition comprising a *Lactobacillus* bacteria is a step of applying an oil layer to the bacteria or composition.

An eleventh aspect of the invention provides a freeze-dried composition of the first aspect. Suitably, the freeze-dried composition of the eleventh aspect is produced according to the method of the tenth aspect.

A twelfth aspect of the invention provides a composition of the first aspect at least partially covered by a layer of oil. Suitably, the at least partially oil-covered composition of the twelfth aspect is produced according to the method of the tenth aspect.

BRIEF DESCRIPTION OF THE FIGURES

In order that the invention may be readily understood and put into practical effect, typical embodiments will now be described by way of example with reference to the accompanying figures, wherein.

BRIEF DESCRIPTION OF THE SEQUENCE LISTING

Figure 1:
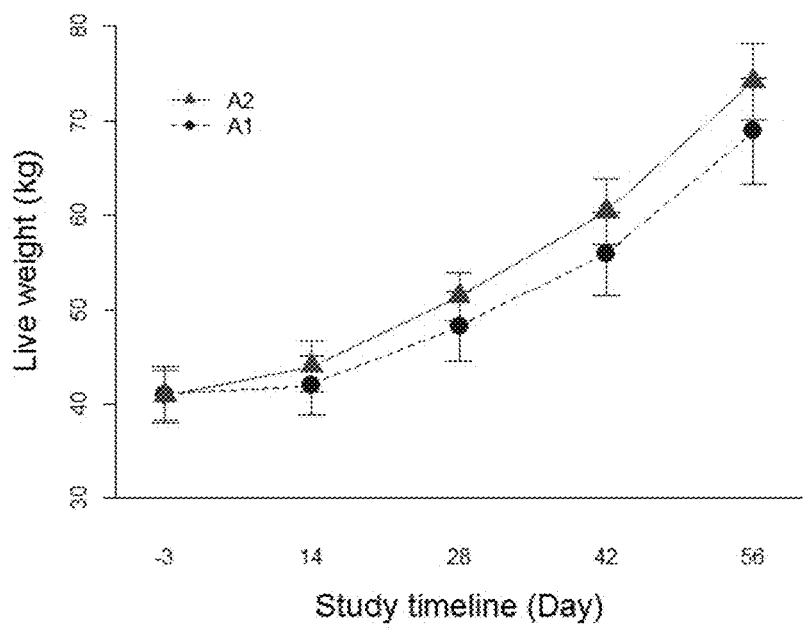
FIG. 1 sets forth line-plots of average live weight (kg) of Experimental Groups A1 (Control Group) and A2 (Treated Group) as a function of Study Timeline (Study Day), as per Example 1 herein. Error bars represent 95% confidence interval.
Figure 2:
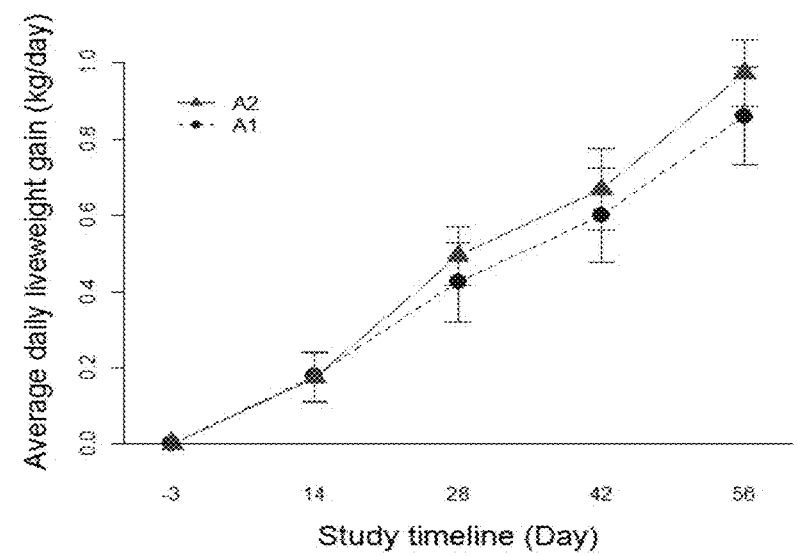
FIG. 2 sets forth line-plots of average daily live weight gain (kg/day) for Experimental Groups A1 (Control Group) and A2 (Treated Group) as a function of Study Timeline (Study Day), as per Example 1 herein. Error bars represent 95% confidence interval.

SEQ ID NOS:1-160: Nucleotide sequences of the genome of *Lactobacillus paracasei* T9 V12/022849.

SEQ ID NOS:161-292: Nucleotide sequences of the genome of *Lactobacillus buchneri* Lb23 V11/022946.

SEQ ID NOS:293-383: Nucleotide sequences of the genome of *Lactobacillus casei* Lz26 V11/022948.

SEQ ID NOS:384-3504: Amino acid sequences of proteins putatively encoded by the genome of *Lactobacillus paracasei* T9 V12/022849.

SEQ ID NOS:3505-6021: Amino acid sequences of proteins putatively encoded by the genome of *Lactobacillus buchneri* Lb23 V11/022946.

SEQ ID NOS:6022-8828: Amino acid sequences of proteins putatively encoded by the genome of *Lactobacillus casei* Lz26 V11/022948.

DETAILED DESCRIPTION

The present invention is at least partly predicated on the determination that certain *Lactobacillus* compositions may offer substantial benefits as supplements for farmed ruminants. In particular, it has been determined that compositions comprising certain combinations of *Lactobacillus* bacteria can exhibit surprising efficacy for use as ruminant animal supplements, particularly cattle supplements.

Accordingly, one aspect of the invention is broadly directed to a composition comprising one or more bacteria of the genus *Lactobacillus*. Typically, the composition comprises a plurality of bacteria of the genus *Lactobacillus*.

It will be understood that bacteria of the composition of this aspect include isolated bacteria. For the purposes of this invention, by "isolated" is meant material (e.g. bacteria, nucleic acids, cells etc.) that has been removed from its natural state or otherwise subjected to human manipulation. Isolated material may be substantially or essentially free from components that normally accompany it in its natural state, or may be manipulated so as to be in an artificial state together with components that normally accompany it in its natural state. Isolated material may be in native, synthetic, or recombinant form. To avoid doubt, as used herein, bacteria of the genus *Lactobacillus* can include isolated bacteria derived from natural or native corresponding *Lactobacillus* bacteria, or synthetic or recombinant bacteria corresponding to natural or native *Lactobacillus* bacteria.

The bacteria of the genus *Lactobacillus* according to the composition of this aspect may be of any suitable *Lactobacillus* species. In embodiments, the bacteria of the genus *Lactobacillus* is of a species selected from the group consisting of *Lactobacillus acetotolerans; Lactobacillus acidifarinae; Lactobacillus acidipiscis; Lactobacillus acidophilus; Lactobacillus agilis; Lactobacillus algidus; Lactobacillus alimentarius; Lactobacillus allii; Lactobacillus alvei; Lactobacillus alvi; Lactobacillus amylolyticus; Lactobacillus amylophilus; Lactobacillus amylotrophicus; Lactobacillus amylovorus; Lactobacillus animalis; Lactobacillus animata; Lactobacillus antri; Lactobacillus apinorum; Lactobacillus apis; Lactobacillus apodeme; Lactoba-* cillus aquaticus; Lactobacillus aviaries; Lactobacillus backii; Lactobacillus bambusae; Lactobacillus bifermentans; Lactobacillus bombi; Lactobacillus bombicola; Lactobacillus brantae; Lactobacillus brevis; Lactobacillus brevisimilis; Lactobacillus buchneri; Lactobacillus cacaonum; Lactobacillus camelliae; Lactobacillus capillatus; Lactobacillus casei; Lactobacillus chiayiensis; Lactobacillus paracasei; Lactobacillus zeae; Lactobacillus catenefornis; Lactobacillus caviae; Lactobacillus cerevisiae; Lactobacillus ceti; Lactobacillus coleohominis; Lactobacillus colini; Lactobacillus collinoides; Lactobacillus composti; Lactobacillus concavus; Lactobacillus coryniformis; Lactobacillus crispatus; Lactobacillus crustorum; Lactobacillus curieae; Lactobacillus curtus; Lactobacillus curvatus; Lactobacillus delbrueckii; Lactobacillus dextrinicus; Lactobacillus diolivorans; Lactobacillus equi; Lactobacillus equicursoris; Lactobacillus equigenerosi; Lactobacillus fabifermentans; Lactobacillus faecis; Lactobacillus faeni; Lactobacillus farciminis; Lactobacillus farraginis; Lactobacillus fermentum; Lactobacillus floricola; Lactobacillus florum; Lactobacillus formosensis; Lactobacillus fornicalis; Lactobacillus fructivorans; Lactobacillus frumenti; Lactobacillus fuchuensis; Lactobacillus furfuricola; Lactobacillus futsaii; Lactobacillus gallinarum; Lactobacillus gasseri; Lactobacillus gastricus; Lactobacillus ghanensis; Lactobacillus gigeriorum; Lactobacillus ginsenosidimutans; Lactobacillus gorilla; Lactobacillus graminis; Lactobacillus guizhouensis; Lactobacillus halophilus; Lactobacillus hammesii; Lactobacillus hamster; Lactobacillus harbinensis; Lactobacillus hayakitensis; Lactobacillus heilongjiangensis; Lactobacillus helsingborgensis; Lactobacillus helveticus; Lactobacillus herbarum; Lactobacillus heterohiochii; Lactobacillus hilgardii; Lactobacillus hokkaidonensis; Lactobacillus hominis; Lactobacillus homohiochii; Lactobacillus hordei; Lactobacillus iatae; Lactobacillus iners; Lactobacillus ingluviei; Lactobacillus insectis; Lactobacillus insicii; Lactobacillus intermedius; Lactobacillus intestinalis; Lactobacillus iwatensis; Lactobacillus ixorae; Lactobacillus japonicus; Lactobacillus jensenii; Lactobacillus johnsonii; Lactobacillus kalixensis; Lactobacillus kefiranofacien; Lactobacillus kefiri; Lactobacillus kimbladii; Lactobacillus kimchicus; Lactobacillus kimchiensis; Lactobacillus kisonensis; Lactobacillus kitasatonis; Lactobacillus koreensis; Lactobacillus kosoi; Lactobacillus kullabergensis; Lactobacillus kunkeei; Lactobacillus larvae; Lactobacillus leichmannii; Lactobacillus letivazi; Lactobacillus lindneri; Lactobacillus malefermentans; Lactobacillus mali; Lactobacillus manihotivorans; Lactobacillus mellifer; Lactobacillus mellis; Lactobacillus melliventris; Lactobacillus metriopterae; Lactobacillus micheneri; Lactobacillus mindensis; Lactobacillus mixtipabuli; Lactobacillus mobilis; Lactobacillus modestisalitolerans; Lactobacillus mucosae; Lactobacillus mudanjiangensis; Lactobacillus murinus; Lactobacillus musae; Lactobacillus nagelii; Lactobacillus namurensis; Lactobacillus nantensis; Lactobacillus nasuensis; Lactobacillus nenjiangensis; Lactobacillus nodensis; Lactobacillus nuruki; Lactobacillus odoratitofui; Lactobacillus oeni; Lactobacillus oligofermentans; Lactobacillus oris; Lactobacillus oryzae; Lactobacillus otakiensis; Lactobacillus ozensis; Lactobacillus panis; Lactobacillus panisapium; Lactobacillus pantheris Lactobacillus parabrevis; Lactobacillus parabuchneri; Lactobacillus paracollinoides; Lactobacillus parafarraginis; Lactobacillus paragasseri; Lactobacillus parakefiri; Lactobacillus paralimentarius; Lactobacillus paraplantarum; Lactobacillus pasteurii; Lactobacillus paucivorans; Lactobacillus pentosiphilus; Lactobacillus pentosus; Lactobacillus perolens; Lactobacillus plajomi; Lactobacillus plantarum; Lactobacillus pobuzihii; Lactobacillus pontis; Lactobacillus porci; Lactobacillus porcinae; Lactobacillus psittaci; Lactobacillus quenuiae; Lactobacillus raoultii; Lactobacillus rapi; Lactobacillus rennanquilfy; Lactobacillus rennini; Lactobacillus reuteri; Lactobacillus rhamnosus; Lactobacillus rodentium; Lactobacillus rogosae; Lactobacillus rossiae; Lactobacillus ruminis; Lactobacillus saerimneri; Lactobacillus sakei; Lactobacillus salivarius; Lactobacillus sanfranciscensis; Lactobacillus saniviri; Lactobacillus satsumensis; Lactobacillus secaliphilus; Lactobacillus selangorensis; Lactobacillus senioris; Lactobacillus senmaizukei; Lactobacillus sharpeae; Lactobacillus shenzhenensis; Lactobacillus sicerae; Lactobacillus silage; Lactobacillus silagincola; Lactobacillus siliginis; Lactobacillus similis; Lactobacillus songhuajiangensis; Lactobacillus spicheri; Lactobacillus sucicola; Lactobacillus suebicus; Lactobacillus sunkii; Lactobacillus taiwanensis; Lactobacillus terrae; Lactobacillus thailandensis; Lactobacillus timberlakei; Lactobacillus timonensis; Lactobacillus tucceti; Lactobacillus ultunensis; Lactobacillus uvarum; Lactobacillus vaccinostercus; Lactobacillus vaginalis; Lactobacillus vermiforme; Lactobacillus versmoldensis; Lactobacillus vespulae; Lactobacillus vini; Lactobacillus wasatchensis; Lactobacillus xiangfangensis; Lactobacillus yonginensis; and Lactobacillus zymae.

In typical embodiments, the bacteria of the genus Lactobacillus is of a species selected from the group consisting of Lactobacillus paracasei, Lactobacillus buchneri, and Lactobacillus casei.

Typically, the composition of this aspect comprises at least two bacterial species selected from the group consisting of Lactobacillus paracasei, Lactobacillus buchneri, and Lactobacillus casei.

In typical embodiments, the composition comprises:
a bacteria of the species Lactobacillus paracasei and a bacteria of the species Lactobacillus buchneri;
a bacteria of the species Lactobacillus paracasei and a bacteria of the species Lactobacillus casei;
a bacteria of the species Lactobacillus buchneri and a bacteria of the species Lactobacillus casei; or
a bacteria of the species Lactobacillus paracasei, a bacteria of the species Lactobacillus buchneri, and a bacteria of the species Lactobacillus casei.

In a typical embodiment wherein the composition comprises a bacteria of the species Lactobacillus paracasei, the bacteria is Lactobacillus paracasei strain T9 as deposited with the National Measurement Institute, Australia, on 14 Dec. 2012 under Accession Number V12/022849, which strain is also referred to herein as Lactobacillus paracasei T9 V12/022849.

In a typical embodiment of the first aspect wherein the composition comprises a bacteria of the species Lactobacillus buchneri, the bacteria is Lactobacillus buchneri strain Lb23 as deposited with the National Measurement Institute, Australia, on 27 Oct. 2011 under Accession Number V11/022946, which stain is also referred to herein as Lactobacillus buchneri Lb23 V11/022946.

In a typical embodiment of the first aspect wherein the composition comprises a bacteria of the species Lactobacillus casei, the bacteria is Lactobacillus casei (formerly Lactobacillus zeae) strain Lz26 as deposited with the National Measurement Institute, Australia, on 27 Oct. 2011 under Accession Number V11/022948, which strain is also referred to herein as Lactobacillus casei Lz26 V11/022948.

In some embodiments, the composition of the first aspect comprises a bacteria selected from the group consisting of

*Lactobacillus parafarraginis; Lactobacillus rapi; Lactobacillus diolivorans; Lactobacillus perolens;* and *Lactobacillus brevis.*

In an embodiment wherein the composition comprises a bacteria of the species *Lactobacillus parafarraginis*, the bacteria is *Lactobacillus parafarraginis* strain Lp18 as deposited with the National Measurement Institute, Australia, on 27 Oct. 2011 under Accession Number V11/022945.

In an embodiment wherein the composition comprises a bacteria of the species *Lactobacillus parafarraginis*, the bacteria is *Lactobacillus parafarraginis* strain N11 as deposited with the National Measurement Institute, Australia, on 14 Dec. 2012 under Accession Number V12/022848.

In an embodiment wherein the composition comprises a bacteria of the species *Lactobacillus rapi*, the bacteria is *Lactobacillus rapi* strain Lr24 as deposited with the National Measurement Institute, Australia, on 27 Oct. 2011 under Accession Number V11/022947.

In an embodiment wherein the composition comprises a bacteria of the species *Lactobacillus diolivorans*, the bacteria is *Lactobacillus diolivorans* strain N3 as deposited with the National Measurement Institute, Australia, on 14 Dec. 2012 under Accession Number V12/022847.

In an embodiment wherein the composition comprises a bacteria of the species *Lactobacillus perolens*, the bacteria is *Lactobacillus perolens* strain TB as deposited with the National Measurement Institute, Australia, on 14 Dec. 2012 under Accession Number V12/022850.

In an embodiment wherein the composition comprises a bacteria of the species *Lactobacillus brevis*, the bacteria is *Lactobacillus brevis* strain TD as deposited with the National Measurement Institute, Australia, on 14 Dec. 2012 under Accession Number V12/022851.

It will be readily understood that bacteria, including bacteria of the genus *Lactobacillus*, comprise bacterial genomes. The skilled person will appreciate that a "genome" of an organism, such as a bacterial organism, refers generally to the complete nucleic acid sequence of the organism.

Generally, as used herein, the term "nucleic acid" designates single- or double-stranded DNA and RNA. DNA includes genomic DNA and cDNA. RNA includes mRNA, RNA, RNAi, siRNA, cRNA and autocatalytic RNA. Nucleic acids may also be DNA-RNA hybrids. A nucleic acid comprises a nucleotide sequence that typically includes nucleotides that comprise an A, G, C, T or U base. However, nucleotide sequences may include other bases such as inosine, methylcytosine, methylinosine, methyladenosine and/or thiouridine, without limitation thereto.

Nucleic acids may, although need not, encode amino acids and/or proteins. Generally, as used herein, by "protein" is meant an amino acid polymer, comprising natural and/or non-natural amino acids, including L- and D-isomeric forms as are well understood in the art.

It will be understood that, as used herein in the context of nucleic acids, proteins, and nucleotide or amino acid sequences thereof, a "fragment" refers to a portion constituting less than 100% of the nucleotide or amino acid sequence. Typically, a fragment comprises at least 1%, 2%, 5%, 10%, 15%, or 20% of the nucleotide or amino acid sequence. More typically, a fragment comprises at least 25%, 30%, 35%, 40%, 45%, or 50% of the nucleotide or amino acid sequence. In some typical embodiments, a fragment comprises at least 55%, 60%, 65%, 70%, 75%, 80%, 85%, 90%, 91%, 92%, 93%, 94%, 95%, 96%, 97%, 98%, or 99% of the nucleotide or amino acid sequence.

It will be understood that, as used herein in the context of nucleic acids, proteins, and nucleotide or amino acid sequences thereof, a "variant" refers to an amino acid or nucleotide sequence in which one or more nucleotides or amino acids have been deleted or substituted by different nucleotides or amino acids. Variants include naturally occurring (e.g., allelic) variants, orthologs (e.g. from other bacteria) and synthetic variants, such as produced in vitro using mutagenesis or genome editing techniques. In embodiments, the variant may have less than 100% but at least 60%, 70%, 75%, 80%, 85%, 90%, 91%, 92%, 93%, 94%, 95%, 96%, 97%, 98%, or 99% sequence identity as compared to an 'original', 'native', or 'wild type' amino acid sequence or nucleotide sequence.

The term "sequence identity" is used herein in its broadest sense to include the number of exact nucleotide or amino acid matches having regard to an appropriate alignment using a standard algorithm, having regard to the extent that sequences are identical over a window of comparison. Thus, a "percentage of sequence identity" is calculated by comparing two optimally aligned sequences over the window of comparison, determining the number of positions at which the identical nucleic acid base {e.g., A, T, C, G, U) occurs in both sequences to yield the number of matched positions, dividing the number of matched positions by the total number of positions in the window of comparison (i.e., the window size), and multiplying the result by 100 to yield the percentage of sequence identity. For example, "sequence identity" may be understood to mean the "match percentage" calculated by the DNASIS computer program (Version 2.5 for Windows; available from Hitachi Software engineering Co., Ltd., South San Francisco, California, USA). A detailed discussion of sequence analysis can be found in Chapter 19.3 of CURRENT PROTOCOLS IN MOLECULAR BIOLOGY, Ausubel, F. M., B. Roger, R. E. Kingston, D. D. Moore, J. G. Seidman, J. A. Smith, and S. Kevin. (2003).

It will be appreciated that, without limitation, nucleic acid and amino acid variants can be created by mutagenising a protein or an encoding nucleic acid, such as by random mutagenesis or site-directed mutagenesis. Examples of nucleic acid mutagenesis methods are provided in Chapter 9 of CURRENT PROTOCOLS IN MOLECULAR BIOLOGY, Ausubel et al, supra which is incorporated herein by reference. Mutagenesis may also be induced by chemical means, such as ethyl methane sulphonate (EMS) and/or irradiation means, such as fast neutron irradiation as known in the art (Carroll et al, 1985, Proc. Natl. Acad. Sci. USA 82 4162; Men et al, 2002, Genome Letters 3 147).

It will be appreciated that nucleic acid or protein variants may also be nucleic acid or protein fragments.

Typically, the genome of the bacteria of the genus *Lactobacillus* of the composition of this aspect comprises a nucleic acid comprising a nucleotide sequence set forth in SEQ ID NOS:1-383, or a fragment or variant thereof.

In typical embodiments as described herein, nucleic acid fragments comprise at least 1%, 2%, 5%, 10%, 15%, or 20%, more typically at least 25%, 30%, 35%, 40%, 45%, or 50%, even more typically at least 55%, 60%, 65%, 70%, 75%, 80%, 85%, 90%, 91%, 92%, 93%, 94%, 95%, 96%, 97%, 98%, or 99% of a nucleotide sequence set forth in SEQ ID NOS:1-383.

In typical embodiments as described herein, nucleic acid variants have at least 60%, 70%, 75%, 80%, 85%, 90%, 91%, 92%, 93%, 94%, 95%, 96%, 97%, 98%, or 99% sequence identity as compared to a nucleotide sequence set forth in SEQ ID NOS:1-383.

Typically, the genome of the bacteria of the genus *Lactobacillus* of the composition of this aspect comprises a nucleic acid encoding an amino acid sequence set forth in SEQ ID NOS:384-8828, or a fragment or variant thereof.

In typical embodiments as described herein, protein fragments comprise at least 1%, 2%, 5%, 10%, 15%, or 20%, more typically at least 25%, 30%, 35%, 40%, 45%, or 50%, even more typically at least 55%, 60%, 65%, 70%, 75%, 80%, 85%, 90%, 91%, 92%, 93%, 94%, 95%, 96%, 97%, 98%, or 99% of an amino acid sequence set forth in SEQ ID NOS:384-8830.

In typical embodiments as described herein, protein variants have at least 60%, 70%, 75%, 80%, 85%, 90%, 91%, 92%, 93%, 94%, 95%, 96%, 97%, 98%, or 99% sequence identity as compared to an amino acid sequence set forth in SEQ ID NOS:384-8828.

In a typical embodiment, the genome of the bacteria of the genus Lactobacillus of the composition of this aspect comprises a nucleic acid comprising a nucleotide sequence set forth in SEQ ID NOS:1-160, or a fragment or variant thereof. Typically, the bacteria is of the species Lactobacillus paracasei.

In a typical embodiment, the genome of the bacteria of the genus Lactobacillus of the composition of this aspect comprises a nucleic acid comprising a nucleotide sequence set forth in SEQ IN NOS:161-292, or a fragment or variant thereof. Typically, the bacteria is of the species Lactobacillus buchneri.

In a typical embodiment, the genome of the bacteria of the genus Lactobacillus of the composition of this aspect comprises nucleic acid comprising a nucleotide sequence set forth in SEQ IN NOS:293-393, or a fragment or variant thereof. Typically, the bacteria is of the species Lactobacillus casei.

In a typical embodiment, the genome of the bacteria of the genus Lactobacillus of the composition of this aspect comprises a genome encoding an amino acid sequence set forth in SEQ ID NOS:384-3504, or a fragment or variant thereof. Typically, the bacteria is of the species Lactobacillus paracasei.

In a typical embodiment, the bacteria of the genus Lactobacillus of the composition of this aspect comprises a genome encoding an amino acid sequence set forth in SEQ ID NOS:3505-6021, or a fragment or variant thereof. Typically, the bacteria is of the species Lactobacillus buchneri.

In a typical embodiment, the bacteria of the genus Lactobacillus of the composition of this aspect comprises a genome encoding an amino acid sequence set forth in SEQ ID NOS:6021-8828, or a fragment or variant thereof. Typically, the bacteria is of the species Lactobacillus casei.

It will be understood that compositions of this aspect may further comprise any other suitable microorganisms, including microorganisms that are, or are not, bacteria of the genus Lactobacillus.

In embodiments, the composition of this aspect further comprises a lactic acid-producing bacteria (LAB), such as a Lactobacillus or Pediococcus species.

In embodiments, the composition of this aspect further comprises an acetic acid-producing bacteria, such as an Acetobacter species. In an embodiment wherein the composition comprises an Acetobacter species, the Acetobacter species is Acetobacter fabarum. In an embodiment, the Acetobacter fabarum species is Acetobacter fabarum strain Af15 as deposited with the National Measurement Institute, Australia, on 27 Oct. 2011 under Accession Number V11/022943.

In embodiments, the composition of this aspect further comprises a yeast, such as a Saccharomyces species or a Candida species. In an embodiment wherein the composition comprises a Candida species, the Candida species is Candida ethanolica. In an embodiments, the Candida ethanolica species is Candida ethanolica strain Ce31 as deposited with the National Measurement Institute, Australia, on 27 Oct. 2011 under Accession Number V11/022944.

It will be appreciated that the composition of this aspect may comprise any suitable concentration of microorganisms or bacteria, such as bacteria of the genus Lactobacillus.

It will be further appreciated that microorganisms and bacteria according to the composition of this aspect, such as bacteria of the genus Lactobacillus, may be live, dead, or inactivated microorganisms or bacteria. Unless the context requires otherwise, as used herein "live" bacteria or microorganisms will be understood to include viable and/or culturable bacteria or microorganisms, as will be understood by the skilled person.

Typically, at least a proportion of the microorganisms of the composition of this aspect, such as bacteria of the genus Lactobacillus, are live, viable, and/or culturable. Typically, at least about: 10%, 20%, 30%, 40%, 50%, 60%, 70%, 80%, or 90% of cells of the microorganisms of the composition of this aspect, such as bacteria of the genus Lactobacillus, are live, viable, and/or culturable.

It will be appreciated that live microorganisms, such as bacteria, within a composition such as the composition of this aspect may replicate and increase in concentration over time. Accordingly, it will be appreciated that concentration of microorganisms, such as bacteria, in the composition of this aspect may vary depending on when the concentration is assessed.

With the preceding in mind, to avoid doubt, the concentration of microorganisms, such as bacteria, as referred to herein may be concentration as measured: directly after production of the composition; directly before administration of the composition to an animal; or directly before addition of the composition to feed, inclusive of food and drink, for consumption by an animal, although without limitation thereto. In a typical embodiment, the concentration of microorganisms, such as bacteria, as referred to herein is concentration approximately twelve hours after production of the composition with the composition being stored at approximately room temperature.

In embodiments, total concentration of microorganisms of the composition of this aspect is at least about $10^5$ colony-forming units per millilitre (CFU/ml) or colony-forming units per gram (CFU/g), at least about $10^6$ CFU/ml or CFU/g, at least about $10^7$ CFU/ml or CFU/g, at least about $10^8$ CFU/ml or CFU/g, or at least about $10^9$ CFU/ml or CFU/g. In embodiments, total concentration of microorganisms is between about $10^5$ CFU/ml or CFU/g and about $10^9$ CFU/ml or CFU/g, or between about $10^6$ CFU/ml or CFU/g and about $10^8$ CFU/ml.

Typically, concentration of each microorganism of the composition of this aspect is at least about $10^5$ CFU/ml or CFU/g, at least about $10^6$ CFU/ml or CFU/g, at least about $10^7$ CFU/ml or CFU/g, at least about $10^8$ CFU/ml or CFU/g, or at least about $10^9$ CFU/ml or CFU/g. In embodiments, concentration of each bacteria of each microorganism is between about $10^5$ CFU/ml or CFU/g and about $10^9$ CFU/ml or CFU/g, or between about $10^6$ CFU/ml or CFU/g and about $10^8$ CFU/ml or CFU/g.

In embodiments, total concentration of bacteria of the genus Lactobacillus of the composition of this aspect is at least about $10^5$ colony-forming units per millilitre (CFU/ml) or colony-forming units per gram (CFU/g), at least about $10^6$ CFU/ml or CFU/g, at least about $10^7$ CFU/ml or CFU/g, at least about $10^8$ CFU/ml or CFU/g, or at least about $10^9$ CFU/ml or CFU/g. In embodiments, total concentration of bacteria of the genus *Lactobacillus* is between about $10^5$ CFU/ml or CFU/g and about $10^9$ CFU/ml or CFU/g, or between about $10^6$ CFU/ml or CFU/g and about $10^8$ CFU/ml or CFU/g.

Typically, concentration of each bacteria of the genus *Lactobacillus* of the composition of this aspect is at least about $10^5$ CFU/ml or CFU/g, at least about $10^6$ CFU/ml or CFU/g, at least about $10^7$ CFU/ml or CFU/g, at least about $10^8$ CFU/ml or CFU/g, or at least about $10^9$ CFU/ml or CFU/g. In embodiments, concentration of each bacteria of the genus *Lactobacillus* is between about $10^5$ CFU/ml or CFU/g and about $10^9$ CFU/ml or CFU/g, or between about $10^6$ CFU/ml or CFU/g and about $10^8$ CFU/ml or CFU/g.

Typically, the composition of this aspect is a liquid composition. More typically, the composition is an aqueous composition, although without limitation thereto.

In some embodiments, the composition may be a solid composition. In embodiments, the solid composition is a powder composition. In some embodiments, the solid composition is in compacted form, such as a pellet or feed biscuit.

It will be appreciated that the composition of this aspect may include any suitable other ingredients, elements, agents, or components. Suitably, in embodiments wherein the composition is a liquid composition, the composition will comprise a liquid solvent. In embodiments wherein the composition is an aqueous composition, the composition will comprise water.

In embodiments, the composition comprises additional microbial components, such as additional bacteria, although without limitation thereto, as hereinabove described.

In embodiments, the composition comprises additional chemical components, such as one or more fillers, carriers, diluents, or excipients.

In a typical embodiment, the composition of this aspect comprises sugar or a sugar syrup. Typically, the sugar or sugar syrup is molasses.

In embodiments, the composition comprises sugar or sugar syrup, typically molasses, at a concentration of at least about 1% weight per weight (w/w) or volume/volume (v/v), such as at least about: 2% w/w or v/v, 3% w/w or v/v, 4% w/w or v/v, 5% w/w or v/v, 6% w/w or v/v, 7% w/w or v/v, 8% w/w or v/v, 9% w/w or v/v, or 10% w/w or v/v. Typically, the sugar or sugar syrup is at a concentration of between about 3 and about 7% w/w or v/v, more typically about 5% w/w or v/v.

In embodiments, the composition of this aspect comprises an acid, typically an organic acid such as humic acid or fulvic acid. In an embodiment, the composition comprises fulvic acid.

In embodiments, the composition comprises an acid, typically an organic acid such as humic acid or fulvic acid, more typically fulvic acid, at a concentration of at least about 0.1% w/w or v/v, such as at least about 0.2% w/w or v/v, 0.3% w/w or v/v, 0.4% w/w or v/v, 0.5% w/w or v/v, 0.6% w/w or v/v, 0.7% w/w or v/v, 0.8% w/w or v/v, 0.9% w/w or v/v, or 10% w/w/ or v/v. Typically, the acid is at a concentration of between about 0.2% w/w or v/v and about 0.6% w/w or v/v, more typically about 0.4% w/w or v/v such as 0.38% w/w or v/v.

Compositions provided according to this aspect of the invention are typically for, suitable for, or when used for administration to an animal. The animal may be any suitable animal, as set out in further detail hereinbelow. Typically, the animal is a farm or livestock animal, more typically a ruminant farm or livestock animal. In typical embodiments, the animal is selected from the group consisting of cattle, sheep, and goats. More typically, the animal is cattle. In a typical embodiment, the cattle is a calf.

Typically, compositions provided according to this aspect are for administration to an animal to improve or enhance one or more characteristics of the animal. The characteristic may be any suitable characteristic, as set out in further detail hereinbelow. Typically, the one or more characteristics are selected from the group consisting of nutrition, growth, development, and productivity. In one typical embodiment, the characteristic is productivity for meat production. In one typical embodiment, the characteristic is productivity for milk production.

As hereinabove described, compositions of this aspect typically comprise live microorganisms, such as bacteria of the genus *Lactobacillus*. However, in some alternative embodiments the microorganisms, such as bacteria of the genus *Lactobacillus*, may be provided in predominantly dead or inactivated form. For example, in some alternative embodiments, the microorganisms, such as bacteria, of the composition may be substantially inactivated by heat or irradiation or other suitable treatment.

Additionally, although less typical, a related aspect of the invention provides a composition derived from the composition as hereinabove described, wherein microorganisms, such as the bacteria of the genus *Lactobacillus*, are substantially removed. By way of non-limiting example, a composition according to this related aspect may be or comprise a culture filtrate of the composition of the aspect hereinabove described.

Another aspect of the invention provides a method of supplementing an animal, such as supplementing the diet or nutrition of an animal, including a step of administering a composition comprising a bacteria of the genus *Lactobacillus* to the animal.

Still another aspect of the invention provides a method of improving or enhancing one or more characteristics of an animal, including a step of administering a composition comprising a bacteria of the genus *Lactobacillus* to the animal.

Typically, the composition administered to the animal according to the method of the above aspects is the composition of the preceding aspect.

The animal to which the composition is administered according to the method of the above aspects may be any suitable animal. Typically, the animal is a non-human animal. Alternatively, the animal may be a human. In embodiments, the animal is selected from the group consisting of livestock, including horses, mules, cattle, sheep, goats, buffalo, oxen, llamas, alpacas, and camels; poultry, including ducks, chickens, turkeys, geese, guinea fowl, and pigeons; companion animals, including dogs, cats, rabbits, gerbils, hamsters, guinea pigs, fish, and companion birds; and sporting or performance animals, including racehorses, greyhounds, and racing camels.

Typically, the animal to which the composition is administered is a ruminant animal. As will be appreciated by the skilled person, ruminants are mammals typically of the taxon Ruminantia within the order Artiodactyla that, in general terms, are able to acquire nutrients from plant-based food by a process including fermentation using specialised stomach structure.

In embodiments, the ruminant animal is selected from the group consisting of bovines, including anoa, auroch, banteng, bison, bongo, buffalo, cattle or cows, ox, eland, four-homed antelope, gaur, gayal, kéwel, kudu, kouprey, imbabala, nildai, nyala, saola, sitatunga, tamaraw, water buffalo, wisent, yak, and zebu; ovines, including argali, bighorn sheep, domestic sheep, mouflon, snow sheep, trinhorn sheep, and urial; caprines including ibex, tahr, bharal, chamois, domestic goat, goral, serow, markhor, mountain goat, muskox, takin, tur, and wild goat; and deer, including elk, barasingha, brocket, chital, huemul, moose, muntjac, pudd, caribou, taruca, and thamin.

Typically, the ruminant animal is selected from cattle, sheep, and goats. More typically, the ruminant animal is cattle. In a typical embodiment, the cattle is a calf.

Typically, the step of administering the composition to the animal according to the method of the above aspects includes administering the composition to the digestive tract of the animal. Typically, the composition is consumed voluntarily by the animal, whereby the composition is administered to the digestive tract of the animal.

In one typical embodiment, the step of administering the composition to the animal according to the method of the above aspects includes combining the composition with food for consumption by the animal.

In one typical embodiment, the step of administering the composition to the animal according to the method of the above aspects includes combining the composition with drink for consumption by the animal.

In one typical embodiment, the step of administering the composition to the animal according to the method of the above aspects includes combining the composition with a milk replacer for consumption by the animal.

Typically, the composition administered to the animal according to the method of the above aspects is administered in an amount of at least about 1 to at least about 100 ml or g per day, or at least about: 2, 3, 4, 5, 6, 7, 8, 9, 10, 15, 20, 35, 30, 35, 40, 50, 60, 70, 80, and 90 ml or g per day. More typically, the composition is administered in an amount of between about 5 and about 35 ml or g per day, such as about 10, 15, 20, 25, and 30 ml or g per day.

Typically, the bacteria of the genus *Lactobacillus* of the composition administered to the animal according to the method of the above aspects is administered in a total amount of at least about $10^5$ CFU per day, or at least about: $10^6$, $10^7$, $10^8$, and $10^9$ CFU per day. Typically, the bacteria of the genus *Lactobacillus* is administered in a total amount of between about $10^5$ and about $10^9$ CFU per day, such as about $10^6$ CFU per day, $10^7$ CFU per day, or $10^8$ CFU per day.

Typically, each bacteria of the genus *Lactobacillus* of the composition administered to the animal according to the method of the above aspects is administered in an amount of at least about $10^5$ CFU per day, or at least about: $10^6$, $10^7$, $10^8$, and $10^9$ CFU per day. Typically, each bacteria of the genus *Lactobacillus* is administered in an amount of between about $10^5$ and about $10^9$ CFU per day, such as about $10^6$ CFU per day, $10^7$ CFU per day, or $10^8$ CFU per day.

In typical embodiments of the above aspect providing a method of improving or enhancing one or more characteristics of an animal, the one or more characteristics that are improved or enhanced are selected from the group consisting of nutrition, growth, development, and productivity of the animal.

In a typical embodiment, the improved or enhanced growth of the animal is greater total weight relative to a corresponding animal not administered the composition. Typically, the greater total weight is at least about 5% greater total weight, or at least about: 6%, 7%, 8%, 9%, 10%, 15%, or 20% greater total weight.

In a typical embodiment, the improved or enhanced development of the animal is greater development of gut structure relative to a corresponding animal not administered the composition. In typical embodiments, the gut structure is rumen structure, such as duodenum, reticulum, and/or abomasum structure. In embodiments, the greater development of the gut structure is greater weight of the gut structure or a part thereof, such as at least 5%, 10%, 20%, 30%, 40%, 50%, 100%, 150%, or 200% greater weight of the gut structure of a part thereof.

In a typical embodiment, the improved productivity of the animal is improved meat production from the animal relative to a corresponding animal not administered the composition. Typically, the improved meat production is at least about 1%, 2%, 3%, 4%, 5%, 6%, 7%, 8%, 9%, 10%, 15%, or 20% greater meat production.

In a typical embodiment, the improved productivity of the animal is improved milk production from the animal relative to a corresponding animal not administered the composition. Typically, the improved milk production is at least about 1%, 2%, 3%, 4%, 5%, 6%, 7%, 8%, 9%, 10%, 15%, or 20% greater milk production.

In another less typical embodiment, the improved or enhanced characteristic of the animal may be a health characteristic. In embodiments, improved or enhanced health of the animal may be decreased scours relative to a corresponding animal not administered the composition. Incidence and/or severity of scours may be decreased by at least about 1%, 5%, 10%, 20%, 30%, 40%, 50%, 60%, 70%, 80%, 90%, or 100%.

A further aspect of the invention provides a supplemented animal produced according to the method of supplementing an animal as hereinabove described. Typically, the supplemented animal is a ruminant animal. More typically, the supplemented animal is cattle, such as a calf.

A still further aspect of the invention provides an animal with one or more improved or enhanced characteristics produced according to the method of improving or enhancing one or more characteristics of an animal as hereinabove described. Typically, the animal with one or more improved or enhanced characteristics is a ruminant animal. More typically, the animal with one or more improved or enhanced characteristics is cattle, such as a calf.

Yet a further aspect of the invention provides an animal product produced by or derived from the supplemented animal or the animal with one or more improved or enhanced characteristics according to the above aspects. The animal product may be any suitable animal product.

In embodiments, the animal product is food or a food product. In embodiments, the food or food product is selected from the group consisting of blood, bone, connective tissue, a dairy product, an egg or egg product, gelatin, cysteine, a meat or meat product, offal, oil, rennet, and whey. Typically, the food or food product is meat or diary. In embodiments, the diary product is selected from the group consisting of milk, cream, cheese, and yoghurt.

In embodiments, the animal product is a non-food product. In embodiments, the non-food product is selected from the group consisting of blood, bone, fibre, fur, lanolin, leather, manure, oil, and wool. Typically, the non-food product is leather or wool.

Still another aspect of the invention provides an animal feed comprising a composition as hereinabove described. The animal feed may be any suitable animal feed. Typically, the animal feed is a ruminant animal feed. The animal feed may be grass and/or hay or the like, such as silage or baleage; pelletised or compacted animal feed products; or liquid feed products, as are well-known in the art. In a typical embodiment, the animal feed is a milk replacer, typically adapted for feeding of calves.

Yet other aspects of the invention relate to the formulation of compositions as herein described, or components thereof.

One such aspect of the invention provides a composition as hereinabove described, or a component thereof, that has been freeze-dried. Typically, the freeze-dried composition or component will further include a cryoprotectant. In embodiments, the cryoprotectant comprises a milk product, such as a milk powder. In embodiments, the cryoprotectant comprises a sugar, such as a disaccharide sugar. Freeze-dried compositions, or components thereof, of this aspect may be in e.g. powder form, or in pellet, feed biscuit, or otherwise compacted form. The freeze-dried composition or component thereof may comprise other suitable ingredients, such as whey, sodium silico aluminate, maltodextrin, calcium carbonate, mineral oil, sodium bicarbonate, sodium chloride, molasses, vegetable protein, corn flour, and/or cellulose, although without limitation thereto.

Another aspect of the invention provides a composition as hereinabove described, or a component thereof, formulated under oil. Suitably, a layer of oil will be applied to constrain or prevent interaction, exchange, or reaction with an outside environment, such as air or water, with the composition or component thereof. Typically, the oil is a vegetable oil, although without limitation thereto.

Throughout this specification, the aim is to describe typical aspects and embodiments without limiting the invention as disclosed herein to any one aspect, embodiment, or specific collection of features. It will be appreciated that various changes and modifications may be made relative to the exemplary disclosure provided herein without departing from the present invention.

In this specification, the indefinite articles "a" and "an" are not to be read as singular indefinite articles or as otherwise excluding more than one or more than a single subject to which the indefinite article refers. For example, "a" microorganism includes one microorganism, one or more microorganisms, and a plurality of microorganisms.

In this specification, the terms "comprises", "comprising", "includes", "including", and similar terms are intended to mean a non-exclusive inclusion, such that a composition or method that comprises or includes a list of elements need not have those elements solely, and may well have other elements not listed.

Where used in this specification, the terms "consisting essentially of" and "consists essentially of" are intended to mean a non-exclusive inclusion only to the extent that, if additional elements are included beyond those elements recited, the additional elements do not materially alter basic and novel characteristics. That is, a composition or method that "consists essentially of" one or more recited elements includes those elements only, or those elements and any additional elements that do not materially alter the basic and novel characteristics of the composition or method.

EXAMPLES

Example 1. Controlled Study of Live Weight in Calves

Introduction

The long-term productivity benefits of improving health and growth of calves in the early stages of development is well documented. A double blinded, controlled, randomized study was conducted to evaluate the efficacy of an exemplary composition as described herein, referred to as "TgM-LB3" on the live weight of pre-weaned dairy calves.

TgM-LB3 Composition

TgM-LB3 as used for this study had the following composition: *Lactobacillus paracasei* strain T9 (Accession Number V12/022849) 10 million CFU per mL ($10^7$ CFU/ml), *Lactobacillus buchneri* strain Lb23 (Accession Number V11/022946) 10 million CFU per mL ($10^7$ CFU/ml), *Lactobacillus casei* strain Lz26 (Accession Number V11/022948) 10 million CFU per mL ($10^7$ CFU/ml), isotonic saline at 0.85% NaCl w/v.

Study Design and Methods

Forty-four clinically healthy Friesian dairy calves (*Bos taurus*) of approximately 3 days of age were randomly split into two equal sized groups: Treated Group (22 calves); and Control Group (22 calves). Calves were housed in individual pens as part of a controlled study design to reduce the risk of cross contamination with commonly occurring health ailments.

All animals were tube-fed colostrum before reaching approximately one day of age. The feeding regime for all animals consisted of milk replacer (Norcovite®, Norco Australia) at 15% of their body weight, fed in a bucket twice a day, plus ad lib access to hay, grain pellets (Calf Starter Crumbles®, Norco Australia), and clean water through the entire period of the Study. With exception to Monensin, there were no feed additives or antibiotics added to the feed.

TgM-LB3 was added to the milk replacer of the Treated Group. A control composition (TgM-Placebo) containing isotonic saline at 0.85% NaCl w/v was added to the milk replacer of the Control Group. Assessments were conducted fortnightly through the study, the assessments concluding when calves reached 56 days of age. At the end of the study, tissue and organ samples were taken from 3 calves in each Group after weaning, for measuring weights of key gastrointestinal organs.

Results

Figure 3:
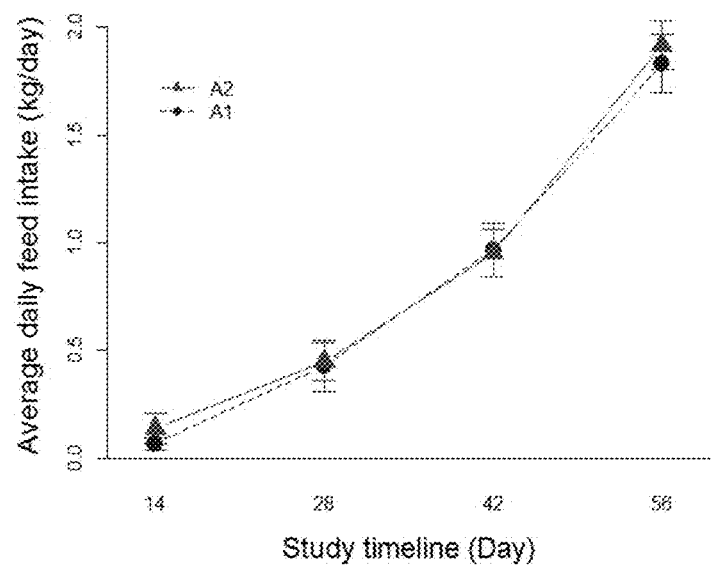
FIG. 3 sets forth line plots of average daily feed intake (kg/day) of Experimental Groups A1 (Control Group) and A2 (Treated Group) as a function of Study Timeline (Study Day), as per Example 1 herein. Error bars represent 95% confidence interval.
Figure 4:
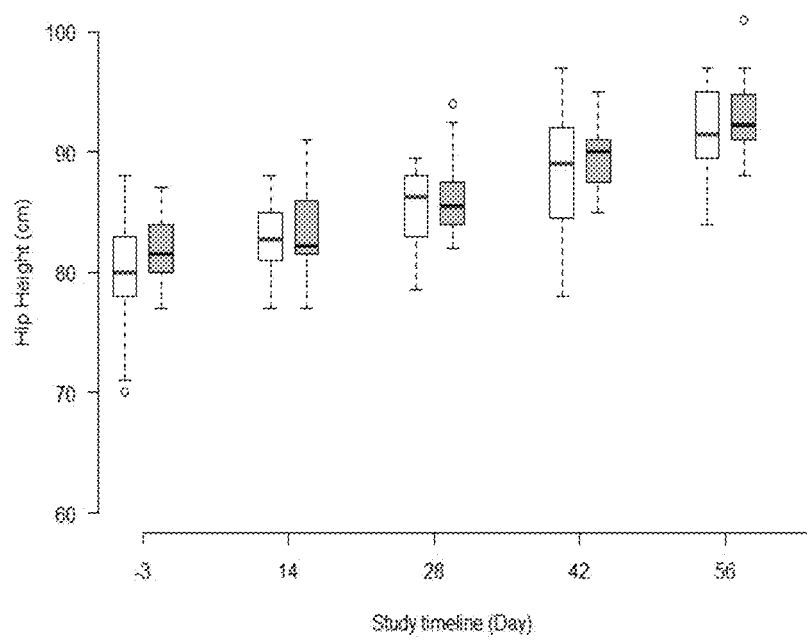
FIG. 4 sets forth box-of-whiskers plots of hip height (cm) of Experimental Groups A1 (white box with red horizontal band; Control Group) and A2 (grey boxes with blue horizontal band; Treated Group) as a function of Study timeline (Study Day), as per Example 1 herein.
Figure 5:
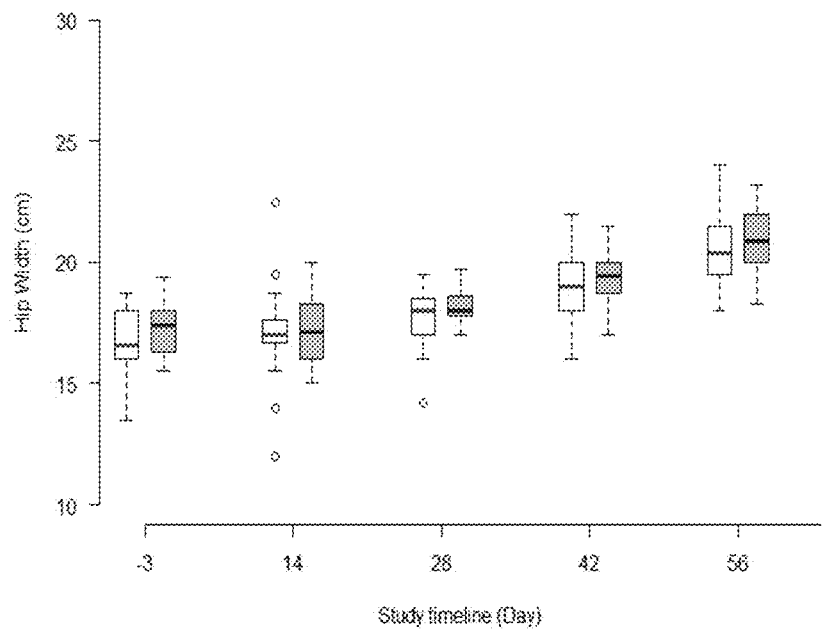
FIG. 5 sets forth box-of-whiskers plots of hip width (cm) of Experimental Groups A1 (white box with red horizontal band; Control Group) and A2 (grey boxes with blue horizontal band; Treated Group) as a function of Study Timeline (Study Day), as per Example 1 herein.
Figure 6:
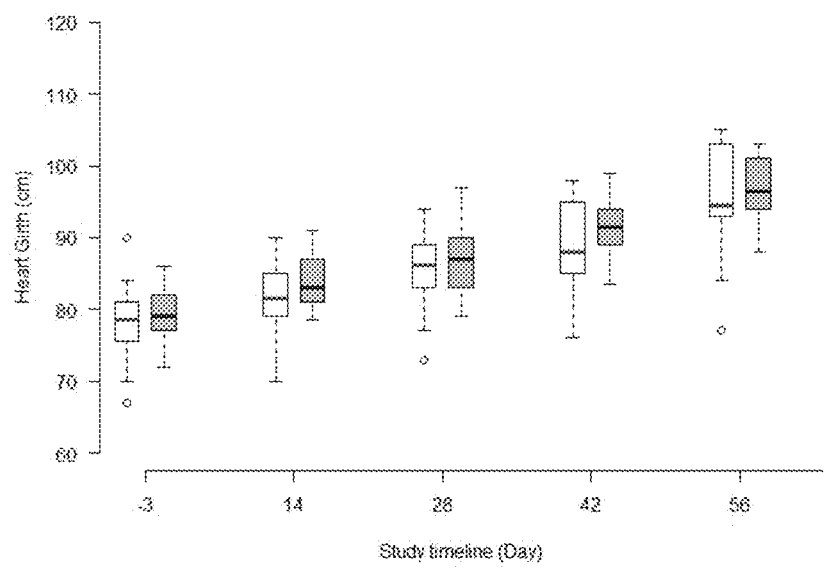
FIG. 6 sets forth box-of-whiskers plots of heart girth (cm) of Experimental Groups A1 (white box with red horizontal band; Control Group) and A2 (grey boxes with blue horizontal band; Treated Group) as a function of Study Timeline (Study Day), as per Example 1 herein.

Calves in the Treated Group were 8.4% heavier, and uniformity of live weights was better, at weaning age compared with calves in the Control Group ($p=0.02$); see FIG. 1 and Table 1. Average and total feed intake did not significantly differ between the groups; see FIG. 3.

Histological examination of the organ tissues of the gastrointestinal tract indicated that TgM-LB3 treated animals exhibited accelerated development of gut structures (Table 2). There was also an observed increase in the surface area of the lining of the gut (Table 3). On average, rumen and intestinal organs folding and crypts in Treated Group calves were greater in length and more dense than in Control Group calves.

Conclusion

Calves in the Treated Group were heavier at weaning (56 days) and had increased development of gastrointestinal tract organs compared with calves from the Control Group. Average and total feed intake did not differ between the groups.

Example 2. Field Trials Assessing Live Weight in Calves

Introduction

Two separate trials were conducted on a commercial dairy farm near Mt Gambier, SA, Australia, running a herd of 650 milking cows. At this dairy, calves are normally grown for a period of 70-90 days or until achieving weaning weights of approximately 120 kg per head. Weaner calves are either kept for future milker replacements or dispatched to other farms for beef production.

Over the calving period, traditionally the first two pens of calves through the operation show good health and growth. The third group onwards are commonly seen to have poorer health and restricted growth rates. The opportunity to run two separate groups one after the other, from the challenging third group onwards, has allowed for performance of a typical composition described herein, referred to as "Mylo", and animal health input costs, to be assessed.

Aim

The trials aimed to determine the effect of Mylo, an exemplary feed supplement as described herein, on the weaning weight of calves, and to observe differences in health indicators of those calves.

Mylo Composition

Mylo as used for this study is prepared as an aqueous solution as follows:
0.38% fulvic acid
5% molasses
$1 \times 10^6$ CFU/mL of each of *Lactobacillus paracasei* strain T9 V12/022849, *Lactobacillus buchneri* strain Lb23 V11/022946, and *Lactobacillus casei* strain Lz26 V11/022948.

The solution containing the above is left to expand overnight at room or ambient temperature of ~23° C.

Design

Each trial used a total of approximately 30 calves (heifers and bulls), divided into two groups of approximately even number. The Treated Groups were given Mylo as a feed supplement and the Control Group was not given Mylo. Each Group was penned then ran in calf paddocks separately for ease of handling and feed management.

Trial Feeding

Calves in the Treated Groups were given 10 mL per day equivalent of Mylo, as an additive to their daily calf milk from the age 4 days to weaning. Control Groups were given the same feeding regime except no Mylo was added to their milk.

Assessment

Calves were weighed close to weaning and ages were recorded. For comparison of weights between groups, live weights were corrected for calf ages at the time of weighing. Average growth rate was estimated after deducting 38 kg (average birth weight) from the live weight of each calf. General health condition of calves was observed and recorded.

Results and Observations: Trial 1

Figure 7:
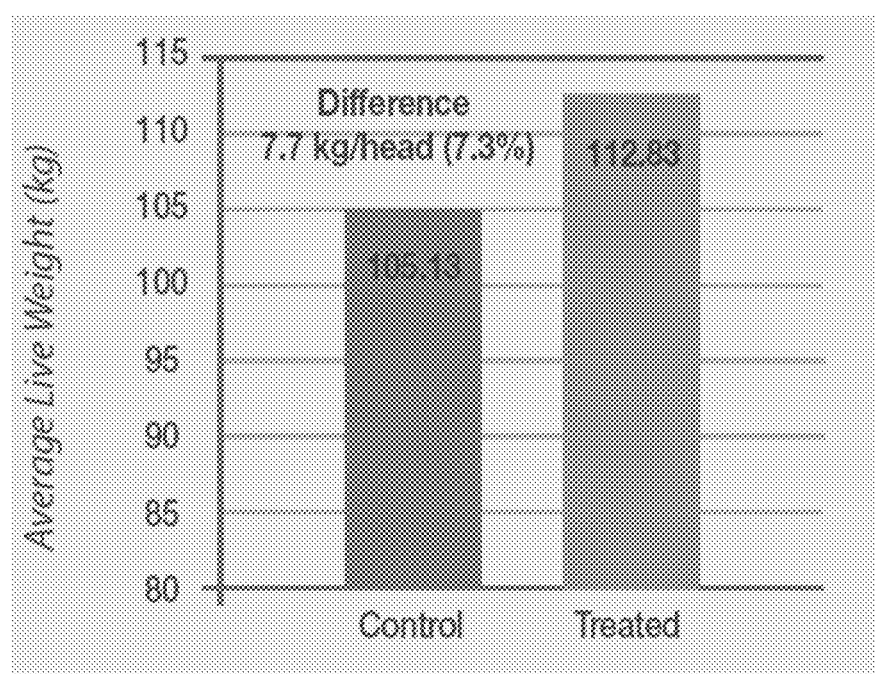
FIG. 7 sets forth average live weight (82 days old) of Control versus Mylo Treated groups, as per Trial 1 of Example 2 herein.

Average live weight of the Treated Group was 7.7 kg/head (7.3%) higher than the Control Group (FIG. 7; Table 4). Furthermore, live weights were taken again after 14 days for five of the calves from the Trial Group who weighed less than 120 kg at the time of the initial weighing. During the 14-day period, these calves recorded an average growth rate of 1310 g per day.

Figure 8:
FIG. 8 sets forth images of stages of growth and improvement in health of calf #6949, as per Trial 1 of Example 2 herein.

After the first few weeks of adding Mylo to the feed of the Treated Group, the farm owners observed many notable differences in health indicators compared to the Control Group: reduced scours, visually more energy, improved appearance and more aggressive feeding. One particular calf (#6949), in the Treated Group had an early set back with a heavy case of scours and was in very poor condition. This animal was given 30 mL of Mylo per day for 3 days, compared to the standard amount of 10 mL per day. Having subsequently made a significant improvement in condition this calf recorded the heaviest live weight in the Treated Group, weighing the equivalent of 118 kg at 82 days of age. Stages of this calf's growth and improvement in health over the trial period are shown in FIG. 8.

Results and Observations—Trial 2

Figure 9:
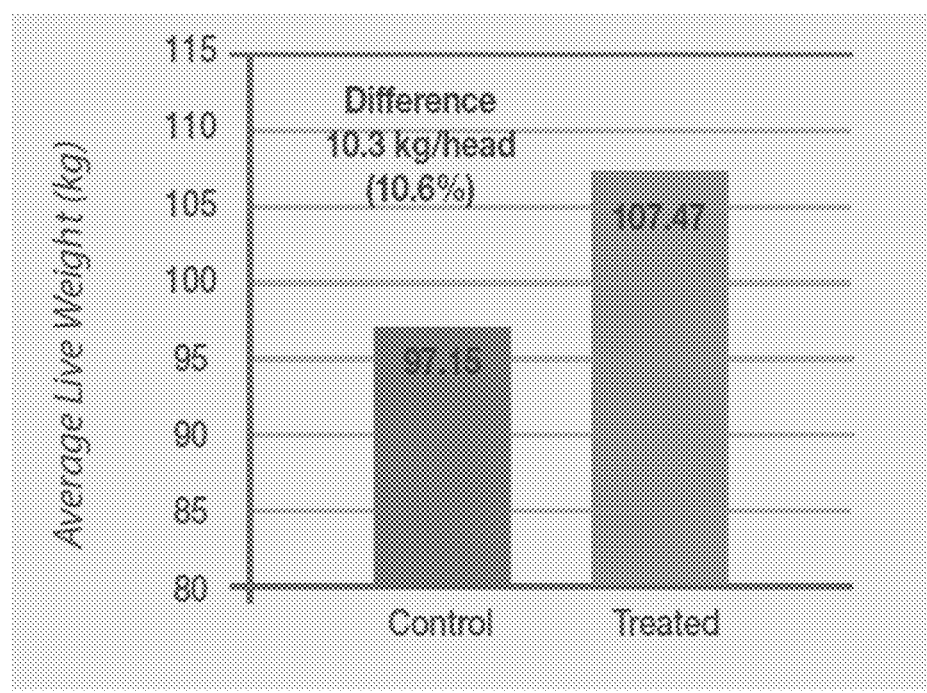
FIG. 9 sets forth average live weight (84 days old) of Control versus Mylo Treated groups, as per Trial 2 of Example 2 herein.

Average live weight of the Treated Group was 10.3 kg/head (10.6%) higher than the Control Group (FIG. 9; Table 5). After the first few weeks of adding Mylo to the feed of the Treated Group, similar observations were made as reported in Trial 1—that is, reduced scours, visually more energy, improved appearance and more aggressive feeding.

An evaluation and comparison of health input costs for the two Groups in this trial was performed, to assess economic benefits of providing Mylo as a feed supplement to improve calf health (Table 6). The Treated Group health costs were AU$16 per head less than the Control Group while the Treated Group achieved 17.4% (123 g/day) superior growth rate, or more than 10% better average live weight by the end of the trial.

Conclusion

A key implication of higher live weights recorded in this study is that calves given Mylo are estimated to reach the target 120 kg live weight at least 10 days earlier than the Control Group. Subsequent savings in feed costs, management time, and health costs are expected to be significant. Furthermore, better development of the gastrointestinal organs, as determined by the controlled study described in Example 1, is expected to confer advantages in health and productivity through maturity.

Example 3. Further Field Study Assessing Live Weight in Calves

Introduction

A trial was conducted on a commercial dairy farm near Meningie, SA, running a herd of 600 milking cows. At this dairy, calves are normally grown for a period of 70-90 days or until achieving weaning weights of approximately 85 kg for Wagyus and 100 kg for Friesians.

Aim

The trial aimed to determine the effect of Mylo on the weaning weight and growth rate of calves, and to observe differences in calf health indicators.

Design

The trial used a total of approximately 17 calves (heifers and bulls), divided into two groups of approximately even number. The Treated Groups were given Mylo as a feed supplement and the Control Group was not given Mylo.

Trial Feeding

Calves in the Treated Groups were given 10 mL per day equivalent of Mylo.

Assessment

Calves were weighed close to weaning and ages were recorded. For comparison of weights between groups, live weights were corrected for calf ages at the time of weighing. The individual birth weights were measured and used for calculating individual gains of each calf.

Results and Observations

Figure 10:
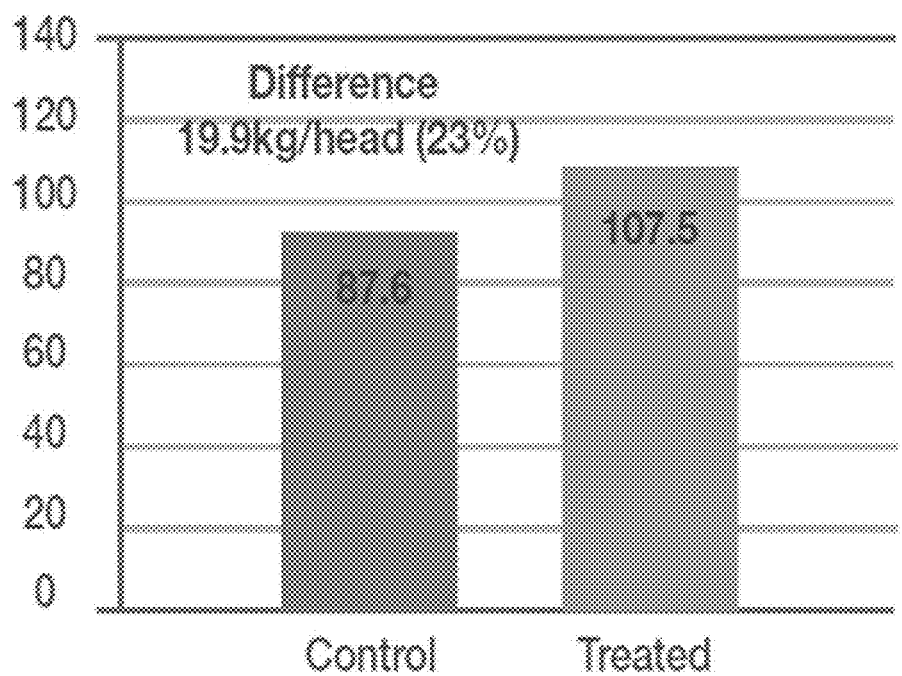
FIG. 10 sets forth average live weight (88 days old) of Control versus Mylo Treated groups, as per Example 3 herein.
Figure 11:
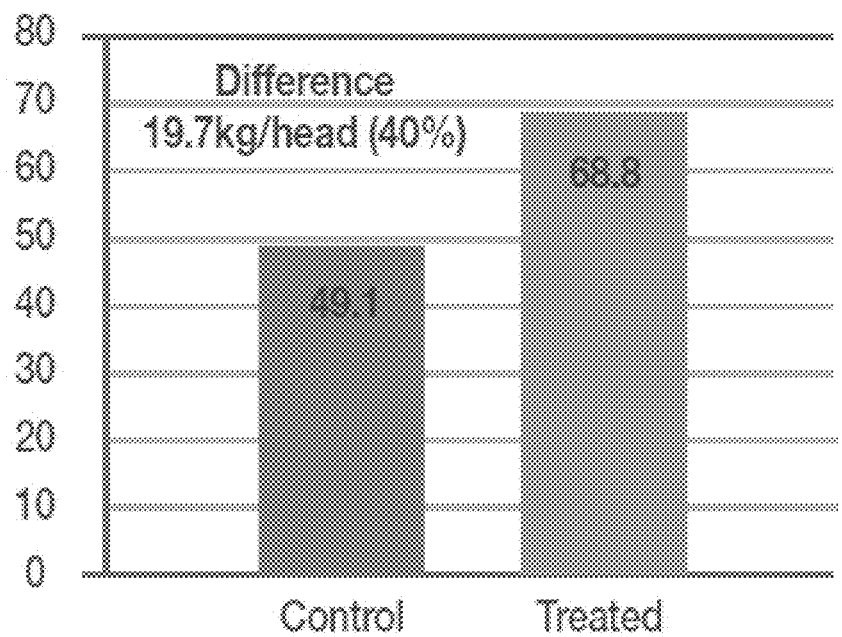
FIG. 11 sets forth average weight gain (88 days old) of Control versus Mylo Treated groups, as per Example 3 herein.
Figure 12:
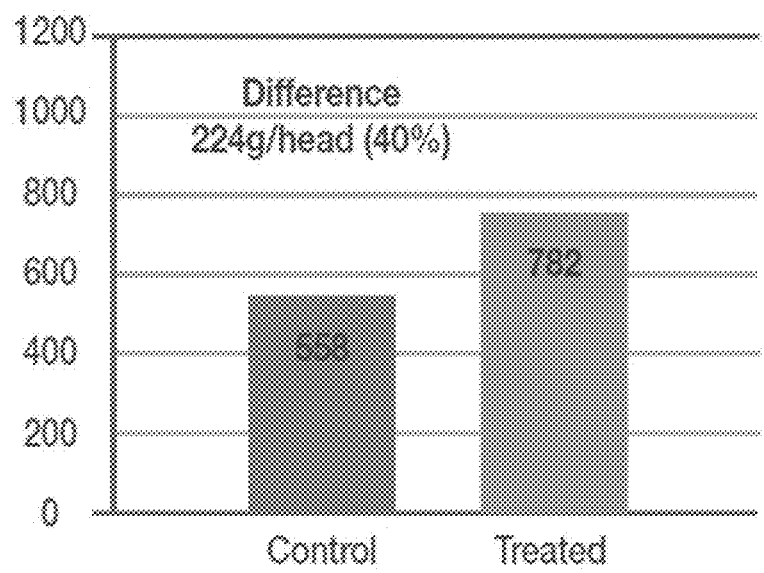
FIG. 12 sets forth average daily weight gain over 88 days of Control versus Mylo Treated groups, as per Example 3 herein.

Average weights and gains recorded for the two groups are shown in FIGS. 10-12. During the trial neither group had received additional animal health treatments. There were noticeable cases of scouring throughout the Control Group unlike the Mylo Treated Group that exhibited no scouring. The difference in scouring incidence may have had a positive effect on the Mylo Treated Group that showed higher weight gain when compared to the Control Group. Calf rearing staff had also noticed significant increase in aggressive feeding habit in the Mylo Treated Group. The calves were more active in nature and the feeding timelines were reduced.

While the difference in daily gain between treatment groups was large, so too was the variability. However, this positive effect on calf weight gain in this trial is consistent with that of previous studies presented herein:
- Gains in weaning weight transfer to benefits in earlier maturity and improved productivity
- Significant reduction in weaning timeline helps to reduce costs associated with fresh milk, milk powder and on farm staffing inputs
- Benefits observed in calf health, and reduced costs of health treatment, add further to the gains in weight Notably, based on positive observations made while conducting the trial, the manager of the dairy decided to treat all remaining and newborn calves with Mylo in place of a previously used powder supplement. In addition to efficacious results, it was considered that Mylo offered benefits due to its easy liquid form and reduced risk of overdosing animals.

Timeline to Target Weaning

Based on the results of this trial, estimated time to weaning was calculated (using extrapolation from average weight gain) for Friesian and Wagyu cattle. Results are presented in Table 7.

Example 4. Alternative Formulations

Formulation details for one typical composition as described herein, referred to as Mylo, are provided in Example 2.

Although Mylo as described in Example 2 is considered particularly desirable in the context of at least some aspects of the present invention, variations of the Mylo formulation may also be desirable.

One variation that may be desirable can be referred to as "Mylo-T9".

Mylo-T9 is prepared as an aqueous solution as follows:
0.38% fulvic acid
5% molasses
$1 \times 10^6$ CFU/mL of each of *Lactobacillus buchneri* strain Lb23 V11/022946, and *Lactobacillus casei* strain Lz26 V11/022948.

The solution containing the above is left to expand overnight at room or ambient temperature of ~23° C.

Another variation that may be desirable can be referred to as "Mylo-fulvic acid"

Mylo-fulvic acid is prepared as an aqueous solution as follows:
5% molasses
$1 \times 10^6$ CFU/mL of each of *Lactobacillus paracasei* strain T9 V12/022849, *Lactobacillus buchneri* strain Lb23 V11/022946, and *Lactobacillus casei* strain Lz26 V11/022948.

The solution containing the above is left to expand overnight at room or ambient temperature of ~23° C.

Example 5. Freeze Dried Compositions

It is considered advantageous in some circumstances to prepare and/or store compositions as described herein, or components thereof, in freeze-dried form.

For this purpose, *Lactobacillus* species may be freeze-dried separately or together. A freeze-drying cryoprotectant is typically used, such as powdered or skimmed milk and/or sugar such as a disaccharide (e.g. sucrose).

The freeze-dried composition may be in powder form, or in the form of a pellet or biscuit. It may be rehydrated in a liquid such as water or milk before use, or added into feed directly. The freeze-dried composition may contain other ingredients such as whey, sodium silico aluminate, maltodextrin, calcium carbonate, mineral oil, sodium bicarbonate, sodium chloride, molasses, vegetable protein, corn flour, cellulose.

Freeze-dried compositions may be particularly desirable for relatively long-term storage and/or transport purposes.

Example 6. Compositions Under Oil

It is considered advantageous in some circumstances to prepare and/or store compositions as described herein, or components thereof, under oil.

For this purpose, *Lactobacillus* species may be placed under oil separately or together, alone or in combination with other components, such as molasses. The composition, or components thereof, may be stored at increased concentration, relative to the composition as administered, or at a concentration for direct administration.

It will be appreciated that if individual components, including *Lactobacillus* species or other components, are stored under oil individually, the components will be mixed to produce a composition prior to or during administration. It will be further appreciated that if the composition or individual components thereof are stored under oil at increased concentration, dilution will be performed prior to or during administration.

The oil used for storage as described in this example will suitably be an oil that is tolerable or acceptable given the intended use of the composition for administration to animals, typically ruminant animals such as cows and calves. Use of vegetable oil is considered appropriate.

Storage of compositions or components thereof under oil may be particularly desirable for relatively long-term storage and/or transport purposes.

TABLES

TABLE 1

Weaning weight at 56 days as per Example 1.

| | Average (kg) |
|---|---|
| Control Group (A1) | 69.18 kg |
| Treated Group (A2) | 75.01 kg |
| Difference Treated-Control | 5.83 kg, 8.4% ($p = 0.02$) |

| Autopsy Results | Treated Group Average Weight (g) | Control Group Average Weight (g) | Difference |
|---|---|---|---|
| Duodenum with digesta | 87 g | 33 g | 54 g, 163% ($p < 0.05$) |
| Abomasum without digesta | 450 g | 390 g | 60 g, 15% ($p = 0.05$) |
| Reticulum without digesta | 357 g | 257 g | 100 g, 39% ($p = 0.05$) |

TABLE 3

Rumen and intestinal organ fold density and length as per Example 1.

| | Control Group (n = 3) | | | Treated Group (n = 3) | | | |
|---|---|---|---|---|---|---|---|
| Variable | Mean (SD) | Median (Q1, Q3) | Min, Max | Mean (SD) | Median (Q1, Q3) | Min, Max | P value |
| Tissue fold density | 1.5 (0.5) | 2.0 (1.0, 2.0) | 1.0, 2.0 | 2.1 (0.8) | 2.0 (2.0, 3.0) | 1.0, 3.0 | 0.09 |
| Tissue fold length | 1.3 (0.5) | 1.0 (1.0, 2.0) | 1.0, 2.0 | 1.8 (0.8) | 2.0 (1.0, 2.0) | 1.0, 3.0 | 0.03 |

Experimental Group

Key:
SD—Standard Deviation,
Q1 & Q3—First and Third Quartiles,
Min—Minimum,
Max—Maximum

TABLE 4

Weight at 82 days as per Trial 1, Example 2.

| | Head | Average Live Weight (kg) | Estimated Average Growth Rate (g/day) |
|---|---|---|---|
| Control Group | 16 | 105.13 | 819 |
| Treated Group | 14 | 112.83 | 913 |
| Difference: Treated-Control | | 7.7 kg (7.3%) | 94 g/day (11.5%) |

TABLE 5

Weight at 42 days.

| | Head | Average Live Weight (kg) | Estimated Average Growth Rate (g/day) |
|---|---|---|---|
| Control Group | 16 | 97.15 | 704 |
| Treated Group | 17 | 107.47 | 827 |
| Difference: Treated-Control | | 10.3 kg (10.6%) | 123 g/day (17.4%) |

TABLE 6

Health costs evaluation. Values in Australian dollars.

| Health Supplements and Treatments | Control Group | | Treated Group | |
|---|---|---|---|---|
| | Head | Cost | Head | Cost |
| Mylo Feed Supplement $0.125/head/day for 84 days | 16 | — | 17 | $178.50 |
| Trisoprim (Antibiotic Treatment) 5 mL × 5 days at $0.20/mL | 5 | $25.00 | 1 | $5.00 |
| Scourban (preventative): 30 mL per dose. Twice/day × 3 days at $0.14/mL | 16 | $403.20 | 0 | — |
| Total Health Cost-by Group | | $428.20 | | $183.50 |
| Total Health Cost per Calf | | $26.80 | | $10.80 |

TABLE 7

Estimated time to weaning.

| Breed | Target Weight | Treated Group | Control Group | Days to Achieve Target Weight |
|---|---|---|---|---|
| Friesian | 100 kg | 76 days | 106 days | Treated Group 30 days quicker |
| Wagyu | 85 kg | 65 days | 89 days | Treated Group 24 days quicker |

SEQUENCE LISTING

The patent contains a lengthy sequence listing. A copy of the sequence listing is available in electronic form from the USPTO web site (https://seqdata.uspto.gov/?pageRequest=docDetail&DocID=US12329181B2). An electronic copy of the sequence listing will also be available from the USPTO upon request and payment of the fee set forth in 37 CFR 1.19(b)(3).

The invention claimed is:

1. A method of improving growth and/or productivity of an animal, including a step of administering at least two bacteria selected from the group consisting of *Lactobacillus paracasei* T9 V12/022849, *Lactobacillus buchneri* Lb23 V11/022946, and *Lactobacillus casei* Lz26 V11/022948 to the animal, and measuring at least one growth and/or productivity characteristic of the animal.

2. The method of claim 1, wherein the bacteria administered to the animal include *Lactobacillus buchneri* Lb23 V11/022946 and *Lactobacillus casei* Lz26 V11/022948.

3. The method of claim 1, wherein the bacteria administered to the animal include *Lactobacillus paracasei* T9 V12/022849, *Lactobacillus buchneri* Lb23 V11/022946, and *Lactobacillus casei* Lz26 V11/022948.

4. The method of claim 1, wherein the animal is administered a composition comprising the at least two bacterial species.

5. The method of claim 4, wherein the concentration of the at least two bacterial species in the composition is at least about $10^5$ CFU/ml or CFU/g, at least about $10^6$ CFU/ml or CFU/g, at least about $10^7$ CFU/ml or CFU/g, or at least about $10^8$ CFU/ml or CFU/g.

6. The method of claim 4, wherein the composition administered to the animal comprises a sugar syrup, wherein a concentration of the sugar syrup in the composition is between about 1% w/w or v/v and about 10% w/w or v/v.

7. The method of claim 1, wherein the animal is a ruminant animal.

8. The method of claim 7, wherein the ruminant animal is a cattle animal.

9. The method of claim 8, wherein the cattle animal is a calf.

10. The method of claim 1, wherein the step of administering the at least two bacterial species to the animal is or includes administering the bacterial species to the digestive system of the animal.

11. The method of claim 10, wherein the at least two bacterial species are combined with feed for consumption by the animal.

12. The method of claim 1, wherein the growth characteristic comprises live weight of the animal.

13. The method of claim 1, wherein the productivity characteristic comprises milk production or meat production.

14. A method of improving the growth rate of an animal, including a step of administering at least two bacteria selected from the group consisting of *Lactobacillus paracasei* T9 V12/022849, *Lactobacillus buchneri* Lb23 V11/022946, and *Lactobacillus casei* Lz26 V11/022948 to the animal, and measuring the growth rate of the animal.

* * * * *